US006249705B1

United States Patent
Snell

(10) Patent No.: US 6,249,705 B1
(45) Date of Patent: Jun. 19, 2001

(54) DISTRIBUTED NETWORK SYSTEM FOR USE WITH IMPLANTABLE MEDICAL DEVICES

(75) Inventor: Jeffery D. Snell, Oak Park, CA (US)

(73) Assignee: Pacesetter, Inc., Sylmar, CA (US)

(*) Notice: Subject to any disclaimer, the term of this patent is extended or adjusted under 35 U.S.C. 154(b) by 0 days.

(21) Appl. No.: 09/422,511

(22) Filed: Oct. 21, 1999

(51) Int. Cl.$^7$ ............................................. A61N 1/37
(52) U.S. Cl. ..................................... 607/59; 607/30
(58) Field of Search ............................. 607/30, 31, 59, 607/60; 128/903, 920

(56) References Cited

U.S. PATENT DOCUMENTS

| | | | |
|---|---|---|---|
| 4,024,875 | 5/1977 | Putzke | 128/419 |
| 4,613,937 | 9/1986 | Batty, Jr. | 364/413 |
| 4,846,180 | 7/1989 | Buffet | 128/419 |
| 5,041,974 | * 8/1991 | Walker et al. | 364/413.27 |
| 5,360,437 | 11/1994 | Thompson | 607/30 |
| 5,456,691 | 10/1995 | Snell | 607/30 |
| 5,456,692 | 10/1995 | Smith, Jr. et al. | 607/31 |
| 5,506,937 | 4/1996 | Ford et al. | 395/12 |
| 5,593,426 | * 1/1997 | Morgan et al. | 607/5 |
| 5,626,630 | * 5/1997 | Markowitz et al. | 607/60 |

FOREIGN PATENT DOCUMENTS

WO 93/06558    4/1993 (WO).

OTHER PUBLICATIONS

Bernstein, Alan D, et al "Recommendations of the NAPE Computer Committee," PACE, vol. 9; pp. 158–163; (Mar.–Apr. 1986).

"Raytel Medical Corporation Introduces Internet Application," Telemedicine Research Center (1996).

Bergelson, M.N., Ph.D "Computerized Pacemaker Follow–up System for Patient Management in Cardiology Practice," Paceart Associates, L.P. (1996).

* cited by examiner

Primary Examiner—William E. Kamm

(57) ABSTRACT

A distributed system of network programmers is described for use with implantable medical devices. The system includes a set of network programmers each having a processor for performing functions directed to programming an implantable medical device and having a transceiver for communicating with the implantable medical device in response to those functions. The system also includes a remotely located network server. The network server has a processor for performing additional functions directed to analyzing information received from the network programmers and to transmitting the results of analyses to selected network programmers. By providing network programmers configured to perform only limited functions in conjunction with a network server, the individual network programmers can be considerably less costly to manufacture and maintain. Yet each of the network programmers can exploit a far greater amount of processing power and access a much larger database of information than a conventional stand-alone programmer. Stored information pertaining to numerous patients is shared among many programmers permitting easy access by the physician. Software updates to the network programmers are easily performed by transmitting new software from the network server to the network programmers. A system of distributed network transtelephonic monitors is also described.

21 Claims, 4 Drawing Sheets

DISTRIBUTED NETWORK SYSTEM FOR USE WITH IMPLANTABLE MEDICAL DEVICES

FIELD OF THE INVENTION

The invention generally relates to programmers and transtelephonic devices for use with implantable medical devices such as pacemakers.

BACKGROUND OF THE INVENTION

A wide range of implantable medical devices are provided for surgical implantation into humans or animals. One common example is the cardiac pacemaker. Another is the implantable cardioverter defibrillator (ICD). Other examples include devices for stimulating or sensing portions of the brain, spinal cord, muscles, bones, nerves, glands or other body organs or tissues. Another example is an implantable drug pump.

Implantable medical devices, particularly pacemakers, are often configured to be used in conjunction with a programmer which allows a physician to program the operation of the pacemaker to, for example, control the specific parameters by which the pacemaker detects arrhythmia conditions and responds thereto. For instance, the programmer may allow the physician to specify the sensitivity with which the pacemaker senses electrical signals within the heart and to further specify the amount of electrical energy to be employed for pacing the heart in circumstances where expected heart signals are not sensed. Additionally, the programmer may be configured to receive and display a wide variety of diagnostic information detected by the pacemaker, such as graphs of electrical heart signals sensed by the pacemaker and responsive pacing signals. Also, the programmer may operate to analyze the data received from the implantable device to assist the physician in rendering diagnoses as to possible arrhythmias and to assist the physician in programming the implantable medical device to provide appropriate therapy.

Traditionally, programmers are stand-alone microprocessor based devices with dedicated program and data storage. Hence, the functions performed by the programmers are limited by the programs and data that are physically stored in the programmer and by the data received from the implanted device. Moreover, historical data pertaining to any particular patient is often stored only in the programmer which was previously used in connection with the patient and it is difficult or time consuming to have the historical data transferred to another programmer. Hence, if a patient visits a different hospital or clinic, previously recorded data for the patient may not be readily available. Hence, it would be desirable to provide a programmer system which could perform more complex analysis functions and which could exploit information databases not physically stored within the programmer. In particular, it would be desirable to provide a programmer which could access collective databases storing historical information for a wide variety of patients.

Also, since programmers are stand-alone devices, it is difficult and costly to upgrade the programmer to provide enhanced features. Typically, to provide new functionality via a software upgrade, each individual programmer must be individually programmed with the new software. As can be appreciated, with a potentially large number of programmers in use, the individual reprogramming of each programmer can be a significant cost. Moreover, problems may arise if some but not all of the programmers are reprogrammed. For example, a physician or other medical professional familiar with the software of one particular programmer may have difficulties if encountering an identical programmer having a different version of the software. Also, it is difficult for a manufacturer to effectively provide software support if different programmers have different versions of the programmer software. Accordingly, it would be desirable to ensure a greater degree of uniformity in the software employed within the programmers by providing a more effective and expedient technique for upgrading the software.

For these and other reasons, stand-alone programmers are typically expensive devices to manufacture and maintain. Similar problems arise with transtelephonic systems for remotely recording electrocardiograms (ECGs) detected by pacemakers. With conventional transtelephonic systems, the patient, while in the home or office, connects electrodes from the wrists, finger tips or chest to a patient transmitter to transmit ECG signals to the telephone receiver. The ECG signals are in turn transmitted via telephone lines to a transtelephonic display device located at a hospital, clinic or physician's office for display and analysis. Typically, the transtelephonic system is employed during patient follow-up sessions subsequent to implantation of the medical device. A technician or other medical professional reviews the ECG signals to verify that the implantable medical device is functioning properly. By employing the transtelephonic device, the patient need not make a visit to the physician's office or clinic every time a follow-up session is required.

As with programmers, transtelephonic display devices are typically stand-alone devices (usually a personal computer) with dedicated programs and data storage. Hence, the functions performed by the transtelephonic ECG display device are limited by the programs and data that are physically stored therein and by the data received telephonically from the patient. Historical ECG data pertaining to a patient is often stored only in the particular transtelephonic ECG display device that was used to receive the data. As with programmers, it would be desirable to provide a transtelephonic display device which could perform more complex analysis functions and which could exploit information databases not physically stored within the device. Also, as with programmers, it is typically time-consuming and expensive to upgrade transtelephonic display devices to provide software with enhanced features and problems can arise if all transtelephonic devices of the same model do not receive the software upgrade.

Currently, there are transtelephonic monitoring devices available which provide a limited capability for accessing collective databases to, for example, generate reports based upon the collective database of a limited patient population. In one example, the collective database can be used to generate reports on one patient or a group of patients to be read using a browser over the Internet. However, as far as the applicant is aware, these systems do not provide for the upgrading of software using a central server and do not perform complex data analysis using a central server. Also, as far as applicant is aware, these systems do not provide for the sharing of any collective data among various device programmers, but rather only among transtelephonic monitoring devices.

Also, conventionally, device programmers and transtelephonic monitoring devices are entirely separate devices with no capability for transmission of data therebetween. Accordingly, it would be desirable to provide an integrated system which can store and share data received from both device programmers and transtelephonic devices and to perform complex analysis based on the stored data. Moreover, the need to provide separate device programmers and transtelephonic monitoring devices results in unnecessary redundancy and expense. Accordingly, it would also be desirable to integrate device programmers and transtelephonic monitoring devices into a single system to eliminate redundancy. In particular, it would be desirable to permit a device programmer to receive and store transtelephonic data initially received at a centralized server.

SUMMARY OF THE INVENTION

In accordance with a first aspect of the invention, a distributed system of network programmers is provided for use with implantable medical devices. The system includes a plurality of network programmers each having a processor for performing essential functions directed to programming an implantable medical device and each having a transceiver for transmitting signals to and for receiving signals from the implantable medical device in response to those functions. The system also includes a network server, located remotely from the plurality of network programmers, provided with a processor for performing functions directed to analyzing information received from the network programmers and to transmitting the results of analyses to selected network programmers. A transmission system is provided for transmitting information between the network server and the network programmers.

In one embodiment, the transmission system includes network interface units in the network server and in the network programmers and a data transmission network interconnecting the network server and the network programmers. The network interface units operate to transmit information over the data transmission network using a transmission protocol selected from a group consisting of X.25, AppleTalk and TCP/IP. The data transmission network is selected from a group consisting of PSTN telephone lines, T1 lines, LANs, WANs, wireless transmission networks, the Internet, and Intranets. The network interface units may be, for example, analog modems, ISDN modems, DSL modems, cable modems, Ethernet interface cards and token-ring interface cards.

In accordance with a second aspect of the invention, a distributed system of network transtelephonic monitors is provided for use with transtelephonic patient transmitters. The system includes a plurality of network transtelephonic monitors each having a transceiver for transmitting signals to and for receiving signals from a remotely-located transtelephonic patient transmitter in response to those functions. The system includes a network server located remotely from the plurality of network transtelephonic monitors provided with a processor for performing functions directed to analyzing the transtelephonic signals. A transmission system is provided for transmitting information between the network server and the network transtelephonic monitors. The network monitor may include means for displaying an ECG received from the transtelephonic patient transmitter. The network server may include means for analyzing the ECG and generating reports based thereon and also for storing the ECGs for numerous patients.

In accordance with a third aspect of the invention, a distributed system of network programmers and network telephonic monitors is provided along with a network server such that a high degree of integration is achieved among the network programmers and network transtelephonic monitors. In accordance with a fourth aspect of the invention, a distributed system of network programmers is provided along with a network server configured to include a transtelephonic transceiver for directly communicating with individual transtelephonic patient transmitters such that separate transtelephonic patient monitors are not necessarily required.

In its various embodiments, the invention permits network programmers or network transtelephonic monitors to be deployed which are typically far less expensive than stand-alone devices yet which exploit a far greater amount of processing power and which access a much larger database of information. Recorded information pertaining to numerous patients is shared among many programmers or transtelephonic devices permitting easy access by the physician. Uniform software updates are easily performed by loading the new software onto the network server, then transmitting the new software to the network programmers or network transtelephonic monitors. Numerous other objects and advantages of the invention are achieved as well. Method embodiments of the invention are also provided.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

Figure 1:
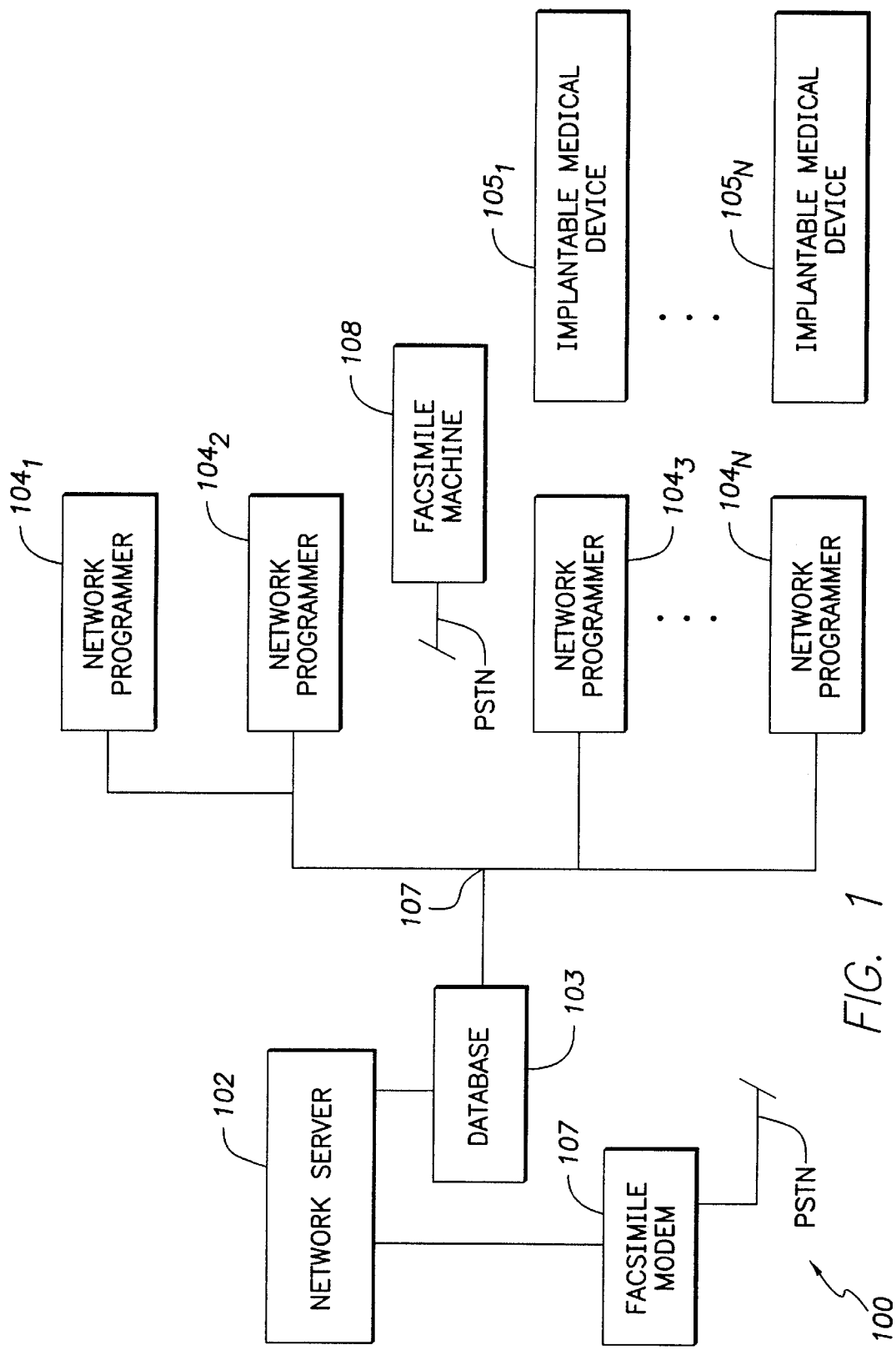
FIG. 1 is block diagram of an exemplary distributed system of network programmers for use with implantable medical devices.

FIG. 1 illustrates a distributed system 100 having a network server 102 with a database 103 and also having a set of network programmers 104 individually denoted $104_1$–$104_N$. The network programmers 104 communicate with the network server 102 via a communication path, e.g., network 107, according to a communication protocol, e.g., X.25, AppleTalk, TCP/IP, etc. Each network programmer includes components for programming the operation of selected implantable medical devices 105 (two of which are shown), such as pacemakers, for transmitting command signals and data pertinent to the implantable medical device 105 to the network server 102, and for receiving and displaying reports and graphs generated by the network server 102 in response to the commands. The network server 102 includes components for receiving commands and data from the network programmers 104, for analyzing data received from the implantable medical devices 105, for generating and transmitting reports and graphs based thereon, and for storing data pertinent to many different patients and different devices in database 103.

Some of the network programmers 104 are provided with printers (not separately shown) for printing out the reports and graphs generated by the network server 102, while others do not. For those network programmers 104 that do not have printers, the network server 102 is controlled, via appropriate commands entered at the network programmer 102, to transmit via telephone lines a copy of reports and graphs displayed on the network programmer 104 using a facsimile modem 107 to a facsimile machine located in the vicinity of the network programmer 104 such that physician may thereby receive a hard copy of the reports. An exemplary facsimile machine 108 is illustrated.

The network programmers 104 may be located, for example, in individual physician offices, clinics, emergency rooms, ambulances, hospital critical care units and the like. The network server 102 may be located, for example, at a hospital administration center, at the headquarters of an HMO or at the offices of the manufacturer of the system. The implantable medical devices 105 are, of course, implanted in various patients that may visit the hospital, clinic etc., having the network programmers 104 to, for example, complete a routine follow-up or to have the implantable device 105 reprogrammed as necessary.

As noted above in the Summary section, by configuring the network programmers 104 to perform only limited functions, the network programmers 104 are therefore considerably less costly to manufacture and maintain than conventional stand-alone programmers. Network programmers 104 provided without printers are even less costly and even more reliable. Yet each of the network programmers 104 can exploit a far greater amount of processing power and access a much larger database of information than typical conventional stand-alone programmers. Stored information pertaining to numerous patients is shared among many network programmers 104 permitting easy access by the physician. Software updates to the network programmers 104 are easily performed by loading new software onto the network server 102, then transmitting the new software to the network programmers 104. Also, because the network programmer 104 performs all actual programming functions, if the link between the network programmer 104 and the network server 102 is broken, the physician can still program the implantable medical device as needed.

By providing a central database 103 associated with network server 102, historical data for individual implantable devices 105 is conveniently stored for use in, for example, producing trend based reports for those devices. The central database 103 also stores entire device population data for use in generating reports contrasting total population against a single device to thereby improve performance predictions, such as longevity predictions. The database also stores clinical protocol information and collects clinical data, as it is acquired, for use in aiding clinical studies, perhaps in connection with efforts to gain FDA approval of new implantable medical devices. During IDE clinical research or other research activities, the clinical researcher (or multiple researchers) can easily participate in an implant, follow-up, EP lab study, etc., remotely via the network 107. Data is captured and examined at a remote location rather than (or in addition to) in the lab while the procedure in progress.

In various other implementations, the network programmer 104 is configured to operate in a stand-alone mode to perform both programming functions and analysis functions as with current state of the art programmers but additionally interfaces with the network server 102 to exploit enhanced data processing capabilities, to access shared databases and to receive software updates. In still other implementations, the network programmer 104 is not capable of performing any programming functions, all of which are controlled by the network server 102. Rather the network programmer 104 operates to receive data from the implantable medical device 105, to receive commands from the physician and to convey the data and commands to the network server. The network server 102 generates all displays and reports and, subject to the physicians control, sends programming commands to the implantable medical devices 105 via the network programmers 104. Several network servers 102 may be employed. In the various embodiments, the network servers 102 may be in one location or may be in multiple locations. The network servers 102 share data either by accessing a common storage unit or by maintaining multiple redundant storage units. Data sharing between the network servers 104 is via the same network 107 used to link to the network programmers 104 or is via an alternate network, or a combination of networks. As can be appreciated, numerous other embodiments may be provided consistent with the general principles of the invention.

Figure 2:
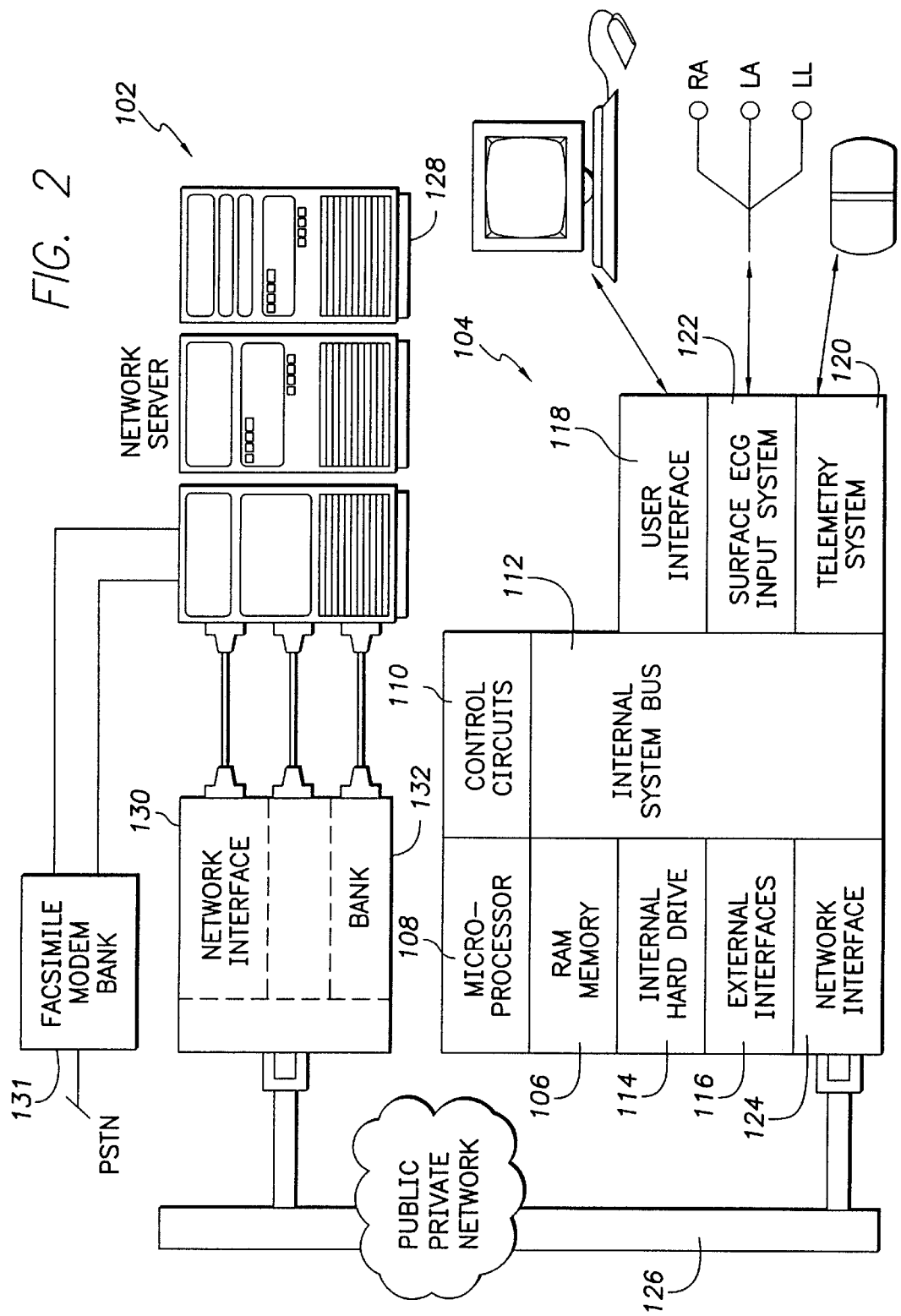
FIG. 2 is block diagram illustrating internal components of one network programmer for use with a pacemaker.

FIG. 2 illustrates pertinent internal components of network server 102 and one network programmer 104 configured to program a pacemaker (not separately shown in FIG. 2). The network programmer 104 includes RAM memory 106, a micro-processor 108, and control circuits 110 such as clocks, interrupt logic, and the like that are necessary for operation of the network programmer 104. The network programmer 104 also includes internal interfaces 112 for data buffering, address decoding, bus arbitration, and the like necessary for interconnection of the various modules. The various modules may include a non-volatile storage device 114 such as hard drive or floppy drive for storing programs and data, one or more external interfaces 116 such as serial/parallel ports for use with printers or modems, and a user interface 118 for interacting with the physician or other user, including a display, buttons, keyboard, touch screen, printer, etc. A telemetry system 120 is provided for receiving data from and for transmitting commands to an implantable medical device mounted 105 within a patient to, for example, program the heart rate or the pacing sensitivity employed by the pacemaker or to receive IEGM signals. An ECG data acquisition unit 122 monitors surface ECG signals. Network programmer 104 also includes a network interface unit 124 for interfacing with a public or private network 126. Network 126, depending upon the implementation, is the public switched telephone network (PSTN), the Internet, local area network (LANs), wide area networks (WANs), wireless transmission networks, or a private network or "Intranet" or any combination thereof. For facsimile transmission the network server 102 includes a bank of one or more facsimile modems 131 which can send reports to remote facsimile machines 108 using a public or private telephone network.

Network server 102 includes a server portion 128 (a processor for performing the aforementioned analysis function and which incorporates the database 103 as shown in FIG. 2) and a network interface unit 130 similar to the interface unit of the network programmer. Network interfaces 124 and 130 are, depending upon the implementation, configured using any standard or proprietary data communications means such as analog modems, ISDN modems, DSL modems, cable modems, Ethernet interfaces, and token-ring interfaces. For implementations wherein modems are employed, network interface 130 of the network server 102 is preferably a rotary bank 132 of modems. The network interfaces 130 are built-in to the network programmer 104 and network server 102 or, in other implementations, are external and are connected via other data communications means such as serial port, SCSI port, parallel port, etc.

The network programmer 104 and network server 102 of FIG. 2 perform the following functions:

1) Data Services

The network server 102 provides data such as text, graphics, programs, files or any combination thereof on-demand to the network programmer 104 based upon commands entered at the network programmer 104. Text and graphics sent from the network server 102 are, depending upon the implementation, e.g., in a format such as PDF, HTML, VRML, or a proprietary format may be used. (PDF is a portable document format provided by Adobe. PDF and Adobe are trademarks.)

2) Database Services

The network server 102 responds to database queries with requested data from database (not separately shown). The network server 102 also updates the database with data provided by the network programmer 104.

3) Computing Services

The network server 102 provides computing services to the network programmer 104, executes programs on-demand utilizing any combination of data provided by the network programmer 104 or accessible by network server 102.

4) Programming Services

The network server 102 provides executable programs, object files, tokenized programs or source code, on-demand, to the network programmer 104. Executable programs are loaded and run directly by the network programmer 104; object files are linked and loaded to run in conjunction with other object files already in the network programmer 104; tokenized programs are executed via an interpreter in the network programmer 104; source code is compiled to object code or to a tokenized form and then executed by the network programmer 104.

5) Non-volatile Storage Updates

The network server 102 provides data to update information in the local non-volatile storage of the network programmer 104 so as to update data and/or programs to newer versions or to add functionality.

6) Security Functions

Appropriate security measures and data integrity checks are employed to ensure the validity of data exchanged between the network programmer 104 and the network server 102. This is desirable for several reasons, including: to maintain data integrity in the network server 102; to maintain data integrity in the network programmer 104; to maintain appropriate safety levels for patients being treated with the network programmer 104; to maintain appropriate configuration controls for network programmers 104, per GMP and international requirements; and to maintain appropriate protection of patient data confidentiality. Security and data integrity checks are implemented using any appropriate combination of hardware and software means—such as communications protocols, handshaking, encryption, etc.

The network server provides additional services as well, including:

1) Facsimile transmission of formatted reports to the referring physician, cardiologist, and other parties.

2) Providing a reliable central storage of long term device performance—available to any physician treating that patient (based on the device serial number).

3) Providing a central storage system for anonymous device performance data—so that patient data confidentiality is not compromised.

4) Providing additional services, by subscription such as late follow-up notification (time since last follow-up exceeds a preset limit), consolidated reports-history of a device, history of a patient, data across a physician's patient population, etc.

Table I provides an exemplary scenario illustrating a typical use of the network programmer 104 by a physician performing a pacemaker follow-up. In this example the network programmer 102 is configured to perform simple interrogation and programming functions stand-alone. All other functions are provided by the network server 102.

TABLE I

| PHYSICIAN | NETWORK PROGRAMMER | NETWORK SERVER |
|---|---|---|
| Turns on the network programmer. | | |
| | Initializes and establishes the network connection, if possible. | |
| | | Responds to the network programmer, and a secure network session is established. |
| Positions the telemetry wand and presses interrogate. | | |
| | Opens a communication channel with the pacemaker via the telemetry system. Reads all programmed settings, counters, and other diagnostic data from the pacemaker via the open telemetry channel. Displays the programmed settings. Transmits interrogated data to the network server. | |
| Selects Max Track Rate parameter for programming. | | |
| | Displays choice of values for Max Track Rate. | |
| Presses HELP to get information about the Max Track Rate parameter. | | |
| | Requests Max Track Rate on-line manual page(s) from the network server. | |
| | | Looks up and sends the Max Track Rate parameter on-line manual page to the network programmer. Customizes the manual page based on the present Mode, Rate, and Refractory settings with graphics and text which illustrate the relationship and possible interactions between these parameters. |
| | Displays the first page. | |
| Presses NEXT PAGE. | | |
| | Displays the next page, which contains "hyper-text links" to related on-line manual pages. | |
| Presses Rate parameter hypertext link. | | |

TABLE I-continued

| PHYSICIAN | NETWORK PROGRAMMER | NETWORK SERVER |
|---|---|---|
| | Requests Rate parameter on-line manual page(s) from the network server. | |
| | | Looks up and sends the Rate parameter on-line manual page to the network programmer. Customizes the manual page based on the present Mode, Max Track Rate, and Refractory settings with graphics and text which illustrate the relationship and possible interactions between these parameters. |
| | Display the new page, which contains a "hyper-text link" to Recommend Timing Parameter Settings. | |
| Presses Recommend Timing Parameter Settings hyper-text link. | | |
| | Requests Recommended timing Parameter settings from the network server. | |
| | | Uses programmed settings, counters, diagnostic data and historic data in the network server database to recommend settings for this pacemaker's timing parameters. Sends a customized on-line manual page with the recommended settings and an explanation of those settings, to the network programmer. |
| | Displays the new page, which contains a "hyper-text link" to Program the Recommend Timing Parameter Settings. | |
| Decides not to change the timing parameters. presses PARAMETERS to return to the programmed settings display. | | |
| | Displays the programmed settings. | |
| Presses MEASURED DATA. | | |
| | Reads measured data from the pacemaker via the open telemetry channel. Transmit measured data to the Network Server. | |
| | | Formats an on-line measured data report with text and graphics describing the battery and lead status, and projected device longevity. |
| | Displays the measured data report. | |
| When the follow-up is complete, presses PRINT FINAL REPORT. | | |
| | Requests a final report from the network server. | |
| | | Formats a final report based on all data acquired during this follow-up and trend data saved from prior follow-ups. A copy is Faxed to the referring physician. Another copy is sent to the network programmer. |
| | Prints the final report. | |
| Turns off the network programmer. | | |

Figure 3:
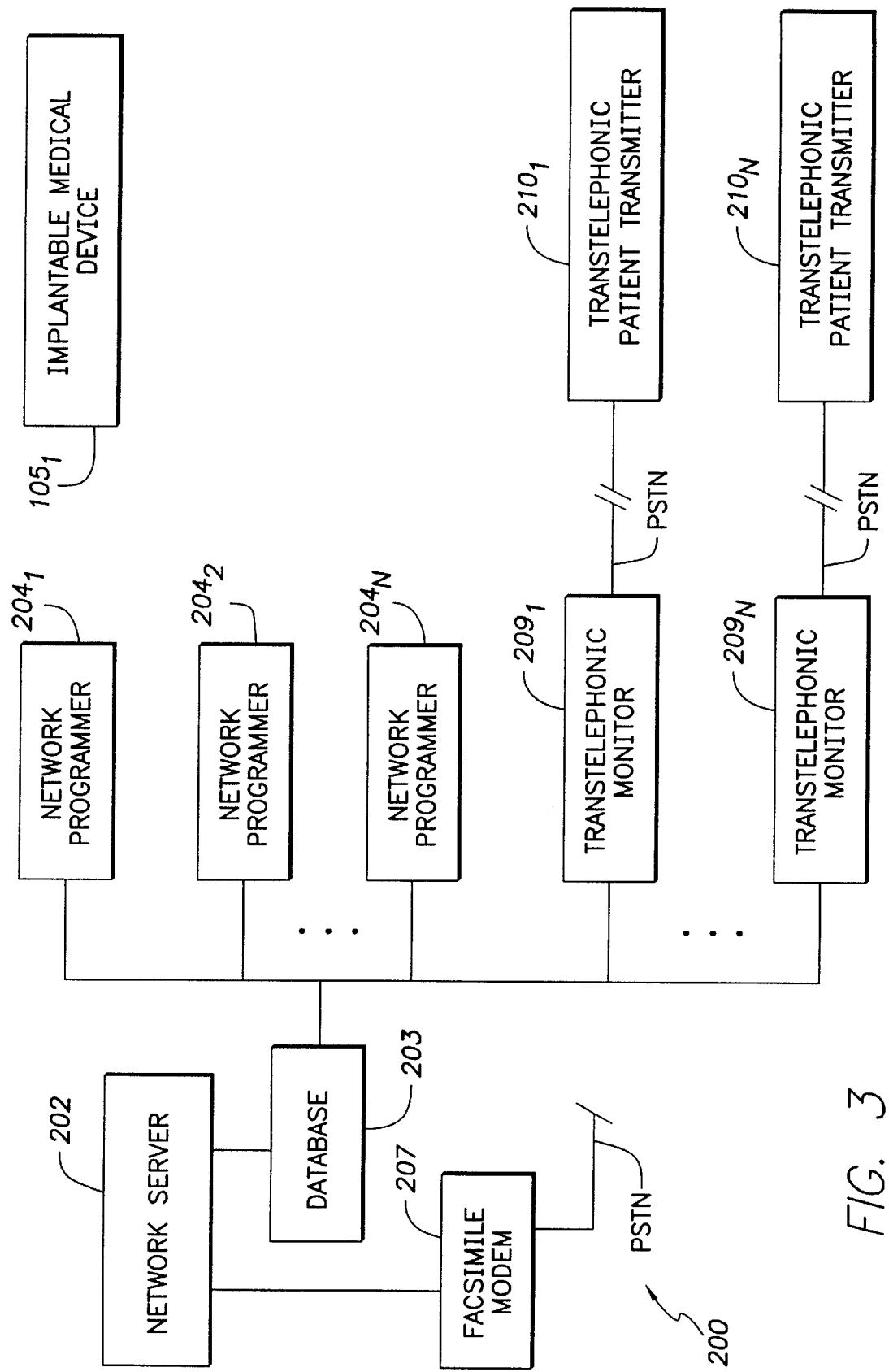
FIG. 3 is block diagram of an exemplary distributed system of network transtelephonic devices for use with implantable medical devices.
Figure 4:
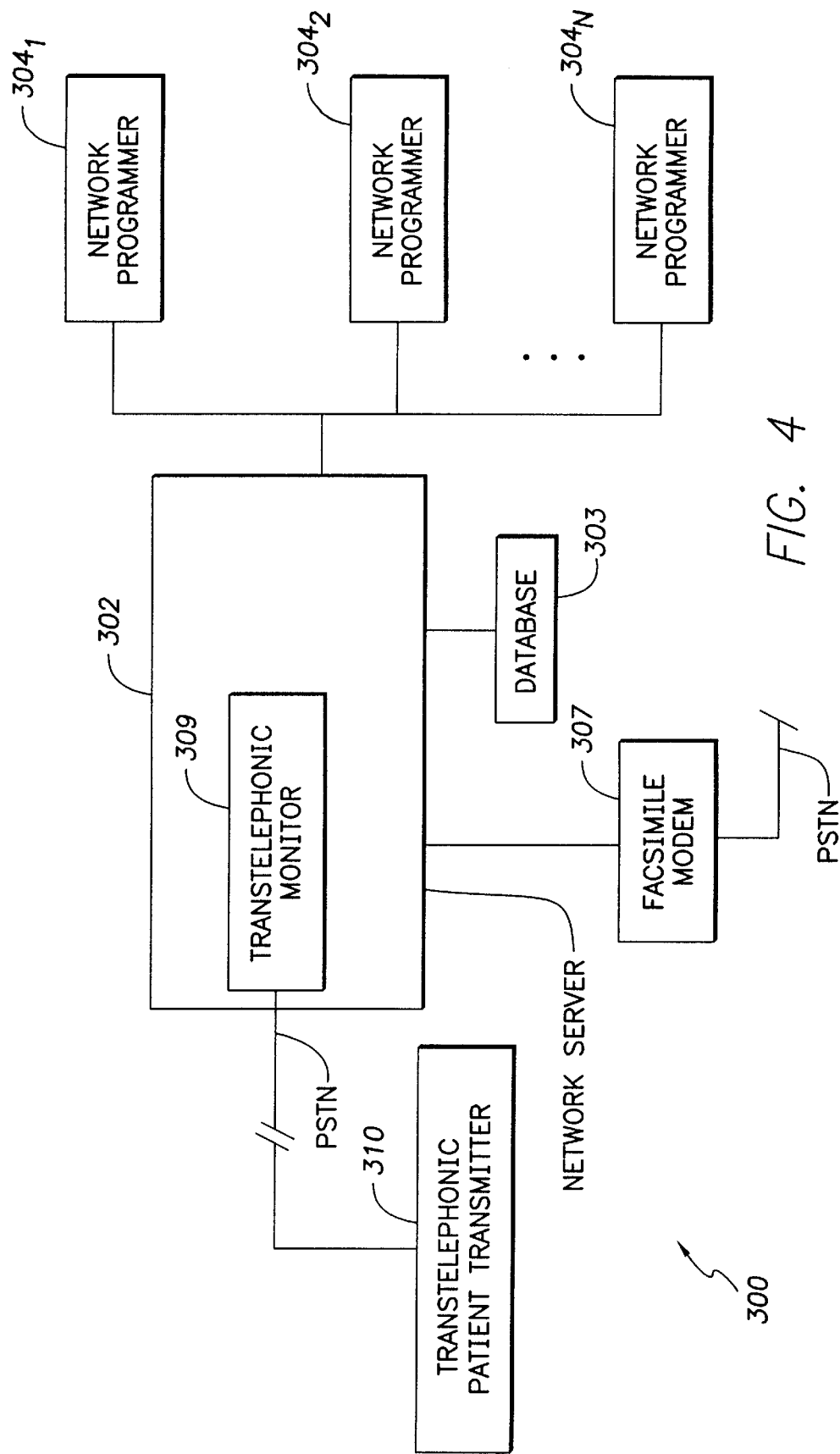
FIG. 4 is block diagram of an exemplary distributed system having a server with an internal network transtelephonic transceiver.

Thus, FIGS. 1 and 2 and Table I illustrate exemplary embodiments of a system of network programmers 104 inter-connected to a network server 102. FIGS. 3 and 4 illustrate two exemplary embodiments of systems additionally including transtelephonic devices. The systems of FIGS. 3 and 4 are similar to those of FIGS. 1 and 2 and only pertinent differences will be described in detail.

FIG. 3 illustrates a network-based system 200 having a network server 202 with a database 203 and having a set of network programmers 204 denoted $204_1$–$204_N$. The system also includes a set of network transtelephonic monitors denoted $209_1$–$209_N$. Each network transtelephonic device 209 includes components for telephonically receiving ECGs and other signals from transtelephonic patient transmitters (denoted 210) via the PSTN, for transmitting command signals and data pertinent to the transtelephonic session to the network server 202, and for receiving and displaying reports and graphs generated by the network server 202 in response to the commands. The network server 202, in addition to including the components described above with respect to FIG. 1, also includes components for receiving commands and data from the network transtelephonic monitors 209, for analyzing data received from the transtelephonic monitors 209, for generating and transmitting reports and graphs based thereon, and for storing data pertinent to many different patients and different devices in database 203. The network transtelephonic monitors 209 may be located, for example, in individual physician offices, clinics, and the like. The network server 202 may be located as described above at a hospital administration center, at the headquarters of an HMO or at the offices of the manufacturer of the system. The transtelephonic patient transmitters 209 are located, for example, in patient's homes, long term care facilities or in a hotel room if carried by a patient while traveling.

As with the network programmers 204, by providing individual network transtelephonic monitors 209 configured to perform only limited functions, the devices are therefore considerably less costly to manufacture and maintain than would otherwise be the case. Yet each of the network transtelephonic monitors 209 can exploit a far greater amount of processing power and access a much larger database of information than typical conventional stand-alone transtelephonic monitors. Stored information pertaining to numerous patients is shared among many transtelephonic monitors 209 permitting easy access by the physician. Software updates are easily performed. Additionally, the network server 202 facilitates transtelephonic follow-up support such as follow-up scheduling and reminder services.

FIG. 4 illustrates a network-based system 300 having a network server 302 with a database 303 and having a set of network programmers 304 denoted $304_1$–$304_N$. The network server incorporates a network transtelephonic transceiver 309. The transtelephonic transceiver portion of the network server 302 includes components for automatically telephonically receiving ECGs and other signals from transtelephonic patient transmitters 310 and for generating reports and graphs in response to the received data. Each network programmer 304 includes components, in addition to those described above, for receiving and displaying reports and graphs generated by the network server in response to the received ECG signals and the like. Hence, additional transtelephonic devices are not required. Rather the network programmer 304 provides access to all of the information otherwise available through the dedicated transtelephonic monitors of FIG. 3.

Conventional transtelephonic patient transmitters transmit an analog signal or tone that varies in accordance with the ECG signal being transmitted. The frequency range for the signal is within the band of normal speech so that it can be transmitted over normal phone lines such as the PSTN. Moreover, for conventional transtelephonic monitoring, it is necessary for a technician performing the monitoring to be able to speak with the patient over the telephone line at various times during a monitoring session. Accordingly, when implemented for use with conventional patient transmitters, the transtelephonic transceiver 309 is preferably configured with a high data rate transceiver capability to adequately process signals transmitted by the patient transmitter and to permit the patient's and the technician's voices to be properly transmitted through the system. In other implementations, transmission between the transtelephonic transceiver 309 and the individual patient transmitters may be performed using other transmission media such as digital transmission media. Moreover, in other implementations, the transtelephonic patient transmitter is configured to transmit the patient's ECG and other signals via the Internet. As can be appreciated, wide range of different transmission media and protocols may be employed.

In yet another embodiment, rather than providing a transtelephonic transceiver within the network server, a separate personal computer or network computer is connected to the network to operate as a transtelephonic monitor and to transmit signals received from individual transtelephonic patient transmitters to the network server. In circumstances wherein a single device will be used exclusively for transtelephonic monitoring, this latter embodiment is advantageous because the personal computer or network computer employed as the transtelephonic monitoring device is typically of lower cost than a network programmer.

What has been described are various distributed networked systems for use with implantable medical devices. The various functional components of the exemplary systems may be implemented using any appropriate technology including, for example, microprocessors running software programs or application specific integrated circuits (ASICs) executing hard-wired logic operations. Although described primarily with respect to an pacemaker, aspects of the invention are applicable to other implantable medical devices, such as ICDs. The exemplary embodiments of the invention described herein are merely illustrative of the invention and should not be construed as limiting the scope of the invention. Accordingly, the scope of the present invention is defined by the following claims.

What is claimed is:

1. A system for use with one or more implantable medical devices, each configured for communicating with a network programmer, wherein the network programmers are additionally configured for communicating with a network server through a communication path, the system comprising:

one or more network programmers each comprising:
　a first processor for performing a first set of functions directed to programming an implantable medical device;
　a first transceiver for communicating with the implantable medical device in response to those functions; and
　a second transceiver for communicating over the communication path; and
a network server located remotely from the network programmers, the network server comprising:
　a second processor for performing a second set of functions directed to analyzing information received from the network programmers; and
　a third transceiver for receiving information and transmitting the results of analyses to selected network programmers via the communication path and the second transceiver of each respective network programmer.

2. The system of claim 1, wherein the second and third transceivers include network interface units in the network programmers and in the network server.

3. The system of claim 2, wherein the network interface units are selected from a group consisting of analog modems, ISDN modems, DSL modems, cable modems, Ethernet interface cards and token-ring interface cards.

4. The system of claim 1, wherein the second and third transceivers operate to transmit information over the communication path using a communication protocol selected from a group consisting of X.25, AppleTalk and TCP/IP.

5. The system of claim 1, wherein the communication path is selected from a group consisting of PSTN telephone lines, T1 lines, LANs, WANs, wireless transmission networks, the Internet, and Intranets.

6. The system of claim 1, wherein the network server is configured to additionally perform the first set of functions.

7. The system of claim 1, wherein one or more of the network programmers is configured to additionally perform the second set of functions.

8. The system of claim 1, wherein one or more of the network programmers includes a printer.

9. The system of claim 1, wherein the network server includes means for transmitting information to facsimile machines.

10. The system of claim 1, further including one or more transtelephonic monitor units interconnected to the network server via the communication path.

11. The system of claim 1, further including a transtelephonic transceiver within the network server.

12. The system of claim 11, wherein the transtelephonic transceiver is configured to receive information directly from one or more transtelephonic patient transmitters.

13. A method for use with one or more implantable medical devices, each configured for communicating with a network programmer, wherein the network programmers are additionally configured for communicating with a network server through a communication path, the method comprising the steps of:

receiving data signals from the implantable medical device using a network programmer;

transmitting the data signals from the network programmer to a network server;

analyzing the data signals received from the network programmer using the network server and transmitting signals representative of the results of the analysis to the network programmer; and displaying the results of the analysis using the network programmer.

14. The method of claim 13, wherein signals are transmitted between the network server and the network programmer using a communication protocol selected from a group consisting of X.25, AppleTalk and TCP/IP.

15. The method of claim 13, wherein signals are transmitted between the network server and the network programmer via a communication path, the communication path selected from a group consisting of PSTN telephone lines, T1 lines, LANs, WANs, wireless transmission networks, the Internet, and Intranets.

16. The method of claim 13, further including the step of transmitting the results of the analysis via facsimile modems.

17. The method of claim 13, wherein a plurality of network programmers are provided.

18. The method of claim 13, further including the steps of:

receiving software programs at the network server, wherein the software programs are configured to enhance the functionality of the network programmers;

transmitting the software programs from the network server to the network programmers; and reprogramming the network programmers using the software programs.

19. The method of claim 13, further including the step of:

generating programming signals for programming the operation of the implantable medical device using the network programmer; and transmitting the programming signals to the implantable medical device from the network programmer.

20. A method for programming a plurality of network programmers each having a processor for performing functions directed to programming implantable medical devices, the method comprising the steps of:

receiving programming software at a network server;

transmitting the programming software to each of the plurality of network programmers from the network server;

reprogramming functionality of each of the network programmers using the programming software received from the network server;

generating programming signals using the programming software for programming the operation of the implantable medical device using the network programmer; and transmitting the programming signals to the implantable medical device from the network programmer for programming functions of the implantable medical device.

21. A method for programming a plurality of network transtelephonic monitors, each having a transceiver for transmitting signals to and for receiving signals from a remotely-located transtelephonic patient transmitter, the method comprising the steps of:

receiving programming software at a network server;

transmitting the programming software to each of the plurality of network transtelephonic monitors from the network server;

reprogramming the functionality of each of the network transtelephonic monitors using the programming software received from the network server; and processing signals transmitted to and received from the remotely-located transtelephonic patient transmitter using the programming software.

* * * * *